(12) United States Patent
Diamandis (10) Patent No.: US 6,261,766 B1
(45) Date of Patent: Jul. 17, 2001

(54) DETECTION OF PROSTATE-SPECIFIC ANTIGEN IN BREAST TUMORS

(75) Inventor: Eleftherios Diamandis, Toronto (CA)

(73) Assignee: Nordion International, Inc. (CA)

( * ) Notice: Subject to any disclaimer, the term of this patent is extended or adjusted under 35 U.S.C. 154(b) by 0 days.

(21) Appl. No.: 08/901,519

(22) Filed: Sep. 26, 2000

Related U.S. Application Data (62) Division of application No. 08/532,808, filed as application No. PCT/CA94/00267 on May 13, 1994, now Pat. No. 5,688,658.

(30) Foreign Application Priority Data

May 14, 1993 (GB) .................................................. 9309966

(51) Int. Cl.[7] .............................. C12Q 3/00; C12Q 1/68; G01N 33/53; G01N 33/567
(52) U.S. Cl. ................................. 435/6; 435/4; 435/7.1; 435/7.21; 435/7.23; 435/63; 435/64
(58) Field of Search .................. 435/6, 7.23, 4, 435/7.1, 7.21; 436/63, 64

(56) References Cited

U.S. PATENT DOCUMENTS

5,688,658 * 11/1997 Diamandis .......................... 435/7.23

FOREIGN PATENT DOCUMENTS

| A2187283 | 9/1987 | (GB) . |
| WOA9201936 | 2/1992 | (WO) . |

OTHER PUBLICATIONS

ACTA Cytologica, vol. 33, No. 6, 1989 F.C. Schmitt, et al., pp. 899–902, "Cytology and Immunocytochemistry of Bilateral Breast Metastases from Prostratic Cancer".

Clinical Biochemistry, vol. 21, No. 3, Jun. 1988, p. 139–150, Diamandis, E.P., Immunoassays with Time–Resolved Fluorescence Spectroscopy: Principles and Applications.

Bas. App. Histochem., vol. 33, 1989, pp. 25–29, M. Papotti et al., "Immunocytochemical Detection of Prostate–Specific Antigen (PSA) in Skin Adnexal and Breast Tissues and Tumors".

Eur. J. Clin. Chem. Clin. Biochem. vol. 29, 1991, pp. 787–794, W.G. Wood et al., "The Establishment and Evaluation of Luminescent–Labelled Immunometric Assays for Prostate–Specific Antigen–alpha1–Antichymotrypsin Complexes in Serum".

Clinical Chemistry, vol. 39, No. 10, 1993, pp. 2108–2114, H. Yu et al., "Ultrasensitive Time–Resolved Immunofluorometric Assay of Prostate–Specific Antigen in Serum and Preliminary Clinical Studies".

* cited by examiner

Primary Examiner—Anthony C. Caputa
Assistant Examiner—Alana M. Harris
(74) Attorney, Agent, or Firm—Banner & Witcoff, Ltd.

(57) ABSTRACT

This invention relates to the detection of prostate-specific antigen (PSA) in female breast tumor extract as a prognostic or predictive indicator for breast carcinoma. The presence of prostate-specific antigen in breast tumours is associated with earlier disease stage, younger women and better survival. PSA is associated with tumors which have estrogen and/or progersterone receptors.

7 Claims, 6 Drawing Sheets

DETECTION OF PROSTATE-SPECIFIC ANTIGEN IN BREAST TUMORS

This application is a division of application Ser. No. 08/532,808, filed Jan. 5, 1996 now U.S. Pat. No. 5,688,658; which is a §371 application of PCT/CA94/00267, filed May 13, 1994, which claimed the benefit of GB 9309966.1, filed May 14, 1993.

FIELD OF THE INVENTION

This invention relates to the detection of prostate- specific antigen (PSA) in female breast tumor extract as a prognostic or predictive indicator for breast carcinoma. The presence of prostate-specific antigen in breast tumors is associated with earlier disease stage, younger women and better survival. PSA is associated with tumors which have estrogen and/or progesterone receptors.

BACKGROUND OF THE INVENTION

Considerable research and related diagnosis has been undertaken in this field of healthcare. In order to facilitate reference to prior art developments and procedures, journal articles are listed at the end of this specification and are hereinafter referenced by number.

Breast cancer is a leading cause of mortality and morbidity among women (1–4). One of the priorities in breast cancer research is the discovery of new biochemical markers which could be used for diagnosis, prognosis and monitoring (4, 5). Breast cancer is one of a few cancers that is dependent on steroid hormones and their receptors. Currently, estrogen and progesterone receptor analysis is performed routinely as an aid in prognosis and selection of therapy (4–6).

Current indicators for diagnosing and monitoring breast tumors include: tumor size, estrogen receptors, progesterone receptors, age, aneuploidy, mitotic activity and Ki67 (29). The prognostic usefulness of these factors depends on their ability to evaluate which patients with breast cancer require aggressive therapeutic treatment and which patients should be monitored.

Mutation of the p53 tumor suppressor gene is one of the most comDonly known genetic defects in human cancer, including breast cancer and results in mutant protein accumulating to high concentrations. Overexpression of p53 protein expression has been found to be an independent predictor of early disease recurrence (29). The accumulation of p53 protein has been found to be an independent marker of shortened survival (30). The majority of tumors that do not produce mutant p53 protein are estrogen and/or progesterone receptor-positive (14).

Prostate cancer is a leading cause of mortality and morbidity among men (7, 8). Prostate tissue and cancer is also dependent on steroid hormones and therapy that takes advantage of this is currently routinely used (9–10). One of the hallmarks of prostate cancer is the appearance in serum, at elevated concentrations, of a 30–33-KD glycoprotein, prostate specific antigen (PSA) (11). PSA is secreted by the epithelial cells of prostatic tissue and is currently widely used as a tumor marker for diagnosing and monitoring prostatic carcinoma.

Previous iuuunohistochemical studies found no PSA immunoreactivity in breast or other tumors (17) or found occasional PSA immunoreactivity with polyclonal but not monoclonal antibodies, suggesting cross-reactivity effects (18). PSA levels in female serum are undetectable in 90% of women. A few women do have traces of PSA which are thought to be produced in the periurethral glands.

We have surprisingly discovered the presence of PSA in breast tumor.

SUMMARY OF THE INVENTION

We have discovered that breast tumors have the ability to produce PSA which can be used as a prognostic indicator. PSA production in breast tumors is associated with estrogen and/or progesterone receptor presence, but not the p53 tumor suppressor gene protein. PSA-positive tumors are associated with younger women and earlier disease state. PSA is a favourable prognostic indicator because it is associated with estrogen and progesterone receptors, with lower disease stage and with improved patient survival. PSA positive tumors respond to endocrine treatment, particularly estrogen receptor-negative tumors.

An object of the invention is in the analysis of PSA in female breast tumor extracts which is useful for prognosis, diagnosis or monitoring.

A significant benefit which follows from this invention is that PSA analysis defines a subgroup of patients which may have a different prognosis from that of other breast tumor patients.

According to an aspect of the invention, a method of detecting PSA in breast tumor extracts to provide a breast tumor prognosis comprises:

a) providing a breast tumor extract from a woman;

b) assaying for the presence of PSA; and c) upon detection of PSA, categorizing the woman as a PSA-positive patient.

According to an aspect of the invention, the PSA positive classification indicates hormonal treatment for the breast tumor condition is required.

According to an aspect of the invention, a method is provided for measuring PSA, based on time-resolved fluorometry (TR-FIA) (12, 13) which is approximately 40-fold more sensitive than the commercially available and widely used immunometric techniques. This method has been thoroughly evaluated and can easily and precisely quantify PSA at levels of 0.05 $\mu$g/L or higher.

In accordance with a preferred aspect of the invention, an ultrasensitive detection method for prostate-specific antigen in breast tumor extract involving time-resolved fluoroimmunoassay is provided. Breast tumor extract is incubated with monoclonal anti-PSA antibody. Biotinylated polyclonal antibody specific to PSA is added to bind to any bound PSA. Alkaline phosphatase-labelled streptavidin (SA-ALP) is added. The activity of ALP is measured by adding the substrate 5-fluorosalicyl-phosphate and then adding $Tb_{3+}$-EDTA to form a fluorescent chelate. Fluorescence is measured during a specific time interval to indicate the presence of PSA. The presence or absence of PSA can be used as a prognostic and predictive indicator of breast carcinoma.

BRIEF DESCRIPTION OF THE DRAWINGS

Preferred embodiments of the invention are demonstrated with respect to the drawings wherein:

FIGS. 1A–C. Analysis of PSA in breast tumor extracts by a TR-FIA method and three immunometric techniques which are currently commercially available. Upper panel: Comparison of TR-FIA with the Hybritech Tandem® PSA kit for 24 breast tumor extracts with PSA >0.3 $\mu$g/L. Middle panel: Comparison of TR-FIA with the DPC IRMA-Count®

PSA kit for the same extracts. Lower panel: Comparision of TR-FIA with the Abbott IM$_x$® assay. The equation represents linear regression analysis and R is the correlation coefficient. one tumor extract sample, not included in the graph, had a PSA value of 61.4 3 μg/L by TR-FIA, 39.4 μg/L by Hybritech and 51.8 μg/L by the DPC kit (not measured by IM$_x$). These data confirm the presence of PSA in breast tumor extracts by four different immunological techniques.

FIG. 5. Proposed scheme for PSA production by breast tumors. Circulating ligands associate with either estrogen, progesterone, androgen or glucocorticoid receptors. The complexes formed act to de-repress the PSA gene. Receptor-negative tumors cannot induce PSA production. The subgroup of tumors which are receptor-positive but do not produce PSA are either deficient in ligands, possess defective receptors or they have a defect downstream from the L-R complex.

DETAILED DESCRIPTION OF THE PREFERRED EMBODIMENTS

We have carried out extensive investigations on breast tumors and surprisingly, found that twenty-nine percent of the breast tumor extracts were found positive for PSA (cutoff level 0.05 μg/L or 0.03 ng/mg total protein). PSA was associated with tumors that were estrogen and/or progesterone receptor-positive (P<0.002). No association was found between PSA levels and levels of the p53 tumor suppressor gene product (P=0.37). High performance liquid chromatography revealed that PSA is present in the tumor in its free, 30 KD form. PSA-positive tumors were associated with younger (premenopausal) women (P=0.012) and earlier disease stage (P=0.064). It appears that PSA production is induced by steroid hormone receptor-ligand complexes.

In accordance with this invention, minute amounts at the molecular level can be relied on to categorize breast tumor patients for a therapeutic regime directed at this type of breast cancer.

The cutoff value of 0.05 μg/L (0.03 ng/mg total protein) for PSA was arbitrarily selected based on the PSA assay sensitivity. PSA values>0.05 μg/L can be easily and precisely quantified by using the developed assay of the invention. It is appreciated that various assay techniques may be used to detect PSA; for example, enzyme immunoassay, radioimmunoassay, chemi- or bio-luminescent immunoassay, fluorescent immunoassay and DNA-based assays to detect expression of the PSA gene at the mRNA level.

In accordance with a preferred aspect of the invention, an assay comprising an ultrasensitive detection method for prostate-specific antigen in breast tumor extract involving time-resolved fluoroimmunoassay is provided. Breast tumor extract is incubated with monoclonal anti-PSA antibody. Biotinylated polyclonal antibody specific to PSA is added to bind to any bound PSA. Alkaline phosphatase-labelled streptavidin (SA-ALP) is added. The activity of ALP is measured by adding the substrate 5-fluorosalicyl-phosphate and then adding $Tb^{3+}$-EDTA to form a fluorescent chelate. Fluorescence is measured over time to indicate the presence of PSA. The presence or absence of PSA can be used as a prognostic and predictive indicator of breast carcinoma. The invention's detection method can also be used for detecting the presence of other markers or substances, such as p53 protein, using the appropriate antibody.

Figure 1A:
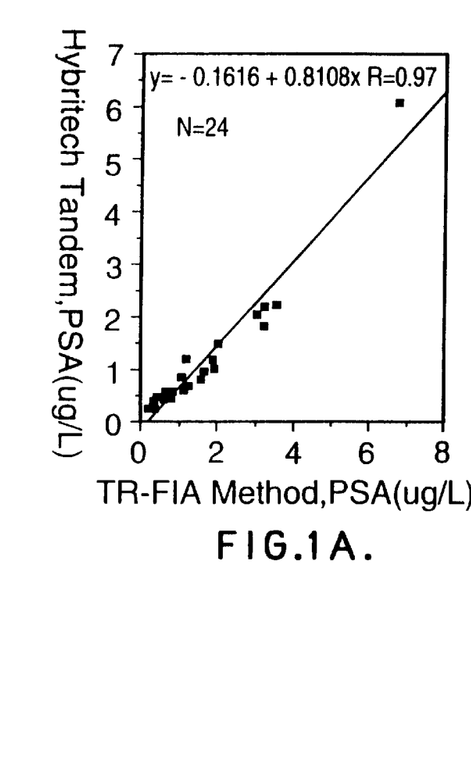
Figure 1B:
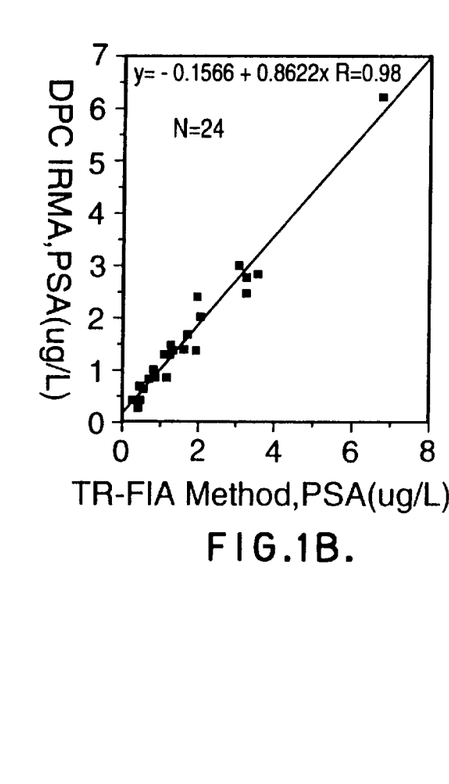
Figure 1C:
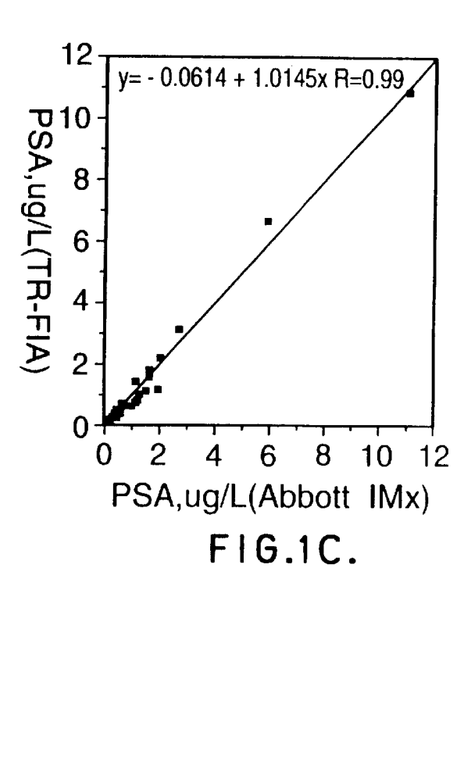

The data we have established and as summarized in Table I, establishes a correlation between breast tumors and tissue level of PSA. 525 breast tumor extracts were analyzed for PSA with the results as shown in Table I. From these tumor extracts, 374 (71.2%) had PSA levels <0.05 μg/L and were considered negative for PSA. One hundred and fifty-one (28.8%) of the tumor extracts had PSA levels>0.05 μg/L, 96 (18.3%) had PSA levels>0.1 μg/L and 49 (9.3%) had PSA levels>0.3 μg/L. Samples with a PSA concentration of >0.3 μg/L, which is potentially measurable by commercial kits, were also analyzed by the Hybritech Tandem® M-R PSA kit, by the IRMA-Count® PSA kit and by the Abbott IM$_x$ Kit. The results are shown in FIG. 1.

To further exclude the possibility of non-specific effects, the assay was repeated for 25 highly positive samples (PSA>0.3 μg/L) under the following conditions: (a) the assay was run in the absence of capture mouse monoclonal anti-PSA antibody (b) the assay was run by using an irrelevant capture mouse monoclonal antibody (against alpha-fetoprotein) (c) the assay was run after substitution of the polyclonal rabbit detection antibody with biotinylated rabbit IgG. In all cases, background signals were obtained verifying that non-specific effects were absent.

Figure 2A:
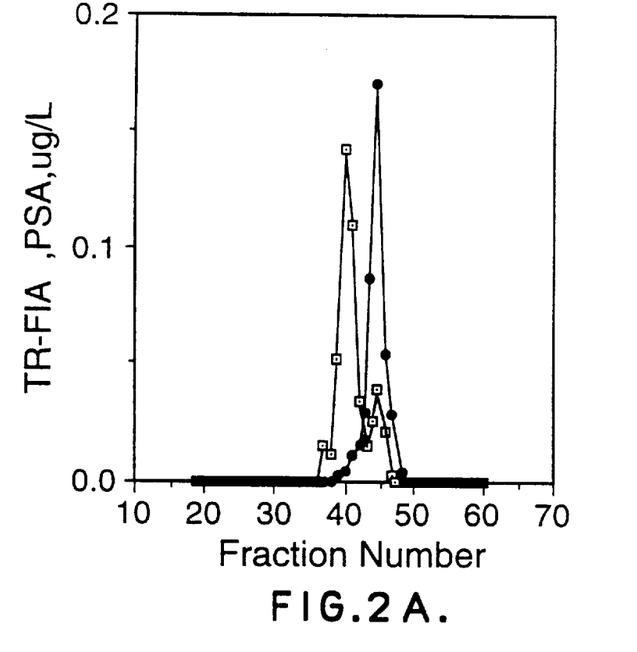
FIGS. 2A–B. Analysis of PSA by TR-FIA in high performance liquid chromatographic (HPLC) fractions. The column was calibrated with a molecular weight standard solution containing thyroglobulin (670 KD), IgG (158 KD), ovalbumin (44 KD), myoglobin (17 KD) and cyanocobalamin (1.4 KD). Upper panel: Breast tumor extract with PSA of 6.7 μg/L by TR-FIA and a male serum sample with 4.27 μg/L of PSA, by TR-FIA. Lower panel: Breast tumor extract with PSA of 61.4 μg/L by TR-FIA. The peak at fraction 45 corresponds to a molecular weight of approximately 30 KD and represents free PSA. The peak at fraction 40 corresponds to a molecular weight of approximately 100 KD and represents PSA bound to $a_1$-antichymotrypsin.
Figure 2B:
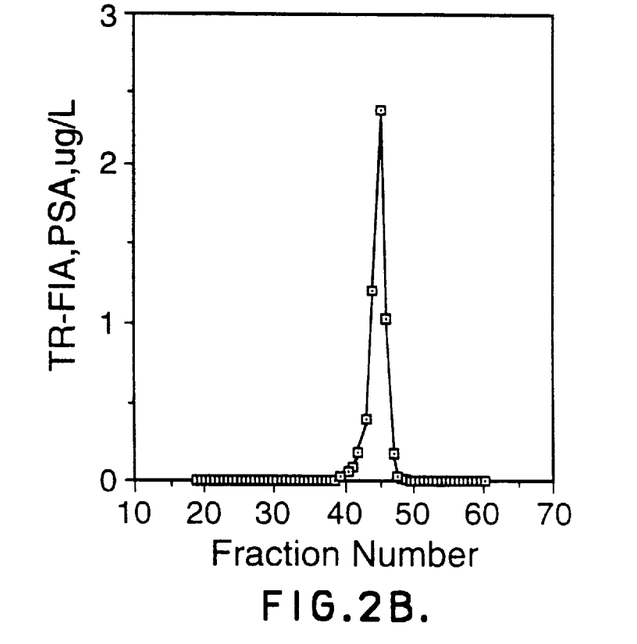

PSA immunoreactivity was further investigated in two breast tumor extracts by using high performance liquid chromatography (HPLC). One male serum sample with a PSA concentration of 4.27 μg/L by TR-FIA and one negative breast tumor extract were used as positive and negative controls. Analysis of PSA was performed in the HPLC fractions and the results are shown in FIG. 2. The PSA-negative breast tumor extract, run between the positive samples, gave undetectable readings in all fractions, in all cases. The PSA immunoreactivity in the two breast tumor extracts, elutes as a single peak at fraction 45 and corresponds to a molecular weight of approximately 30 KD. The PSA immunoreactivity in the male serum sample elutes in two peaks at fractions 40 and 45 and corresponds to molecular weights of approximately 100 KD and 30 KD, respectively. These two peaks correspond to PSA bound to $a_1$-antichymotrypsin and to free PSA, respectively (13,15, 16). These findings demonstrate that the PSA in the breast tumor extracts is present exclusively in the free 30 KD form.

In order to exclude the possibility of contamination of the extracts, six PSA-positive and six PSA-negative breast tumors that were stored frozen at −70° C. were reextracted. Rerun of the fresh extracts with the TR-FIA assay confirmed the original results in all cases. Ninety-four breast tumor extracts were also obtained from another steroid hormone receptor laboratory serving different hospitals in Toronto. From these, 17 (18%), 12 (13%) and 5 (5.3%) had PSA values>0.05, >0.1 and>0.3 µg/L, respectively.

Recovery experiments done by spiking PSA-negative tumor extracts with seminal plasma PSA gave values averaging 83% of the amount of exogenous PSA added. Dilution experiments were performed by diluting a breast tumor extract with a high PSA concentration (20.4 µg/L) with either a 6% (w/v) bovine serum albumin solution or a PSA-negative breast tumor extract. The obtained values, at dilutions ranging from 2 to 32-fold, were very close to those predicted by the PSA-value in the undiluted specimen (100±5%). A batch of 16 breast tumor extracts (four with PSA<0.05 µg/L and twelve with PSA>1 µg/L) were also sent to two different laboratories performing routine PSA assays by the Hybritech and DPC methods. In both cases, their values were very similar to the ones obtained by our method, in our laboratory. These data further demonstrate that the invention's PSA detection results are not due to any non-specific effects and that contamination is very unlikely.

Although we describe detection of PSA with a time-resolved immunofluorometric technique, it is understood that those skilled in the art may use other presents is avaialable or future immunological techiques for PSA quantification to at least 0.03 ng/mg of total protein. For example, techniques capable of such sensitivity include chemiluminescence with acridinium esters as labels, enzymatically triggered chemiluminescence with alkaline phosphatase and dioxetanes substrates luminol chemiluminescence enhanced by horseradish peroxidase, immunoassays using alkaline phosphatase and the fluorogenic substrate 4-methylumbelliferyl phosphate or p-nitrophenyl phosphate, immunoassay using horseradish peroxidase and substrates like ABTS and tetramethylbenzidine and time-resolved immunofluorometric assays with $Eu_{3+}$ as label.

In addition, PSA expression may also be detected by determining whether mRNA for PSA is present in a breast tumor sample. The preferred procedure for detecting mRNA for PSA is by PCR amplification. mRNA is isolated from breast tumor samples and CDNA synthesized by reverse transcription. PCR amplification of cDNA is accomplished using PSA specific primers. A probe is used to detect cDNA for PSA. Other methods for detecting an RNA for PSA may also be used, such as, the Northern Blot technique.

For most of the tumor extract samples analyzed for PSA, data for estrogen (ER) and progesterone (PR) receptor concentrations was available. Also 474 samples were analyzed for the presence of the p53 tumor suppressor gene product, using a method previously described (14). Tumors were then classified as being positive or negative for ER, PR, p53 and PSA using the following negativity cutoff levels:<10 fmol/mg of total protein for ER and PR (14, 30, 31);<3 U/L for p53 (equivalent to 0.02 ng/mL) (14) and<0.05 µg/L for PSA. The data are summarized in Table II.

There is a significant association between the presence of estrogen and/or progesterone receptors and the presence of PSA in the tumors (P<0.002). PSA is independently associated with ER and PR because tumors which are either ER(+) only or PR(+) only still have higher percentage of positivity for PSA in comparison to tumors which are negative for both receptors. Additionally, the highest percentage of PSA-positive tumors is associated with tumors that are positive for both the ER and PR (Table II). There is no association between the presence of PSA and the presence of the p53 tumor suppressor gene product (P=0.37). It has recently been shown that the latter is strongly associated with estrogen and/or progesterone receptor-negative tumors (14) an association also shown in Table II for the samples of this study (P<0.001).

Correlation studies using linear regression analysis between ER and PR and PSA, for all samples of this study (N=525) gave the following Pearson correlation coefficients: r=−0.023, not significantly different from zero (NS), P=0.60 for ER and r=−0.015, (NS), P=0.71 for PR. When only the PSA-positive tumors were used for correlation (N=151) the following Pearson correlation coefficients were obtained: r=−0.015, (NS), P=0.85 for ER and r=−0.068, (NS), P=0.40 for PR.

Some breast tumors had very high PSA levels. Highest values were obtained for five tumors in which PSA levels were>20 µg/L in the extracts and between 200–1000 ng of PSA per g of breast tumor tissue.

Figure 3:
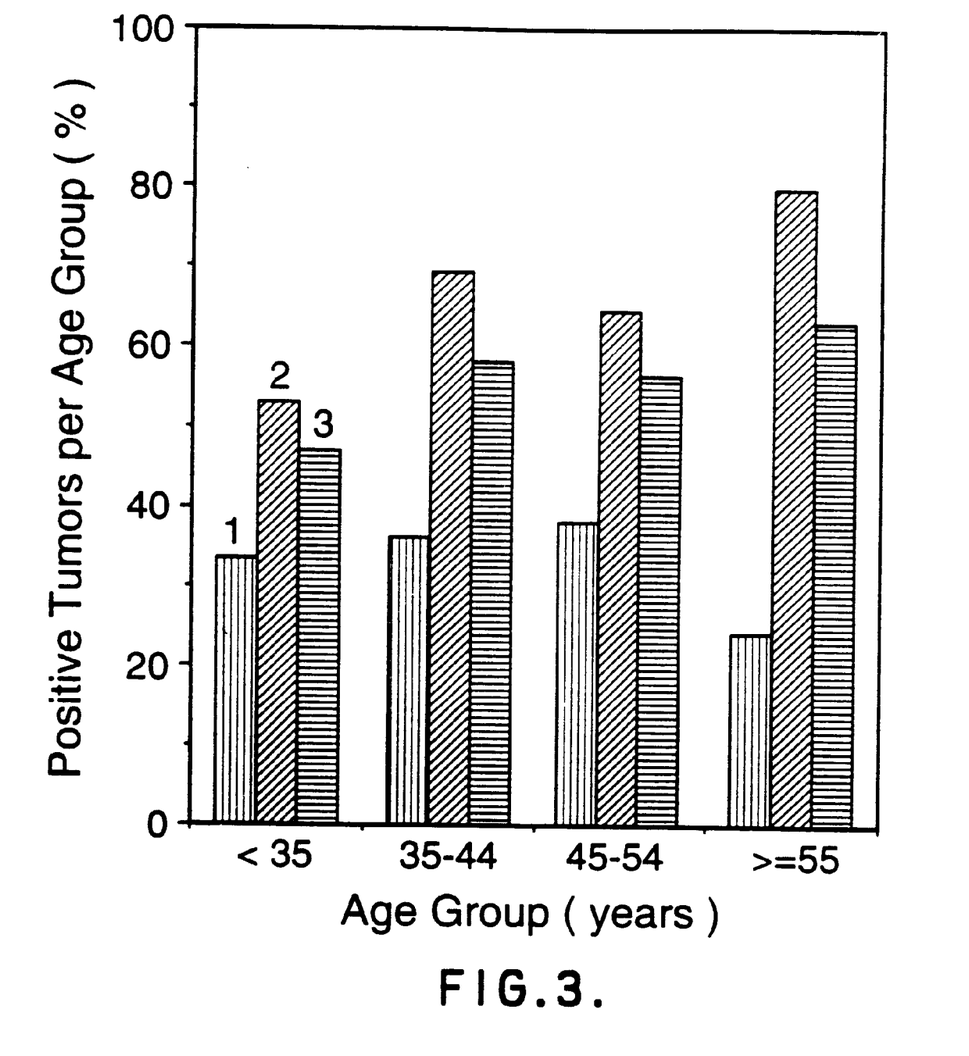
FIG. 3. Percentage of PSA-positive (1), estrogen receptor-positive (2) and progesterone receptor-positive (3) tumors in four groups of patients with age (years) of <35, 35–44, 45–54 and greater or equal to 55. PSA-positive tumors were preferentially distributed among younger patients (P=0.012) and estrogen receptor-positive tumors among older patients (P=0.001). The progesterone receptor-positive tumors were not preferentially distributed in any age group (P=0.45).

Association analysis between PSA presence in breast tumors and patient age gave the results shown in Table III and FIG. 3. PSA was distributed preferentially in younger (premenopausal) patients and this preference was statistically significant (P=0.012).

Figure 4:
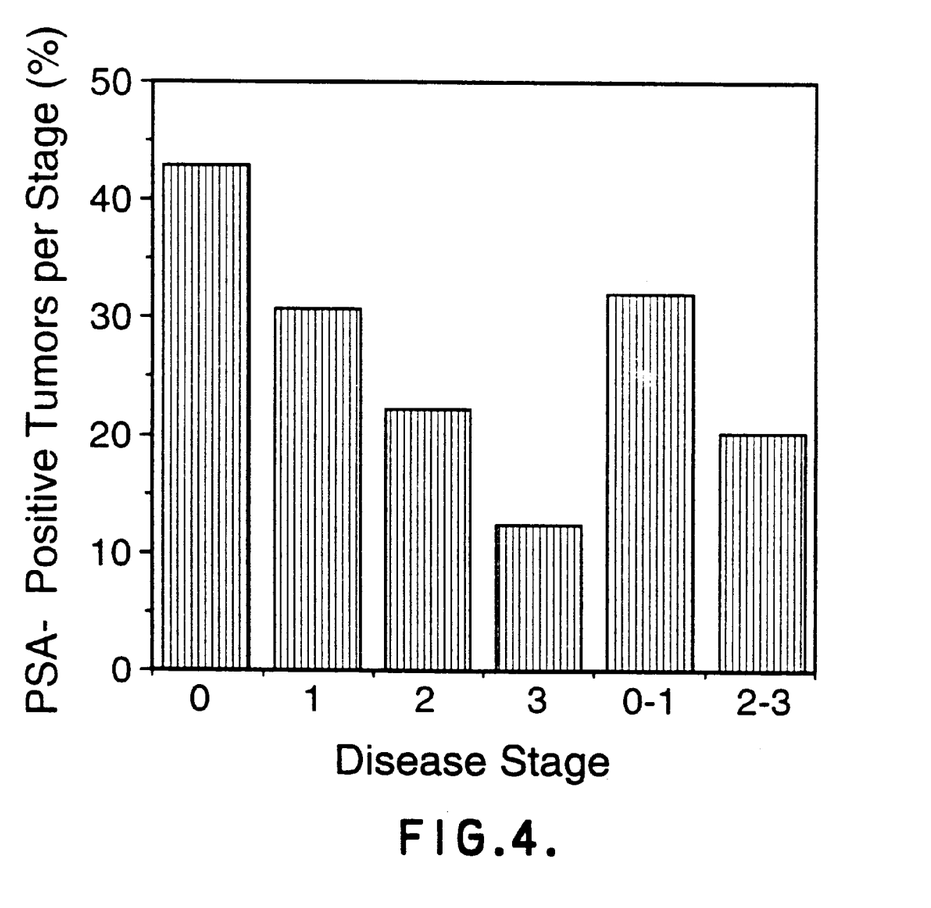
FIG. 4. Percentage of PSA-positive tumors in each disease stage or in stages 0–1 or 2–3. Stages 0–1 indicate a localized tumor and stages 2–3 indicate increased spreading of the tumor. There is a clear trend for PSA-positive tumors to be associated with lower disease stage (see also Table 4).

Tumor stage was available in 203 patients. The results of the distribution of PSA-positive tumors in various stages is given in Table IV and FIG. 4. Clearly, there is a trend for the PSA-positive tumors to be preferentially associated with lower disease stage.

PSA-positive tumors are predominantly ER(+) and PR (+). The presence of PSA in a tumor is indicative of functional ER and PR because PSA is closely associated with the PR (Table V). PR is a product of the action of the ER and is indicative of functional ER. Thus, monitoring PSA would be a useful test to identify patients who possess functional ER and PR. These patients are the ones most likely to respond to endocrine treatment which currently consists of administering one or more of the following: Antiestrogens, antiprogestins, antiandrogens, progestins, androgens, glucocorticoids. Thus, the classificationof patients as PSA(+) and PSA(−) may be useful to select those who will benefit from endocrine treatment.

In addition, a subgroup of PSA-positive and ER- negative patients was suprisingly found to have a good prognosis and respond well to endocrine treatment. In order to examine the prognostic significance of PSA in the subsets of patients who are ER-negative or ER-positive, the hazard ratio between PSA-positive and PSA-negative patients was calculated for two subsets being the ER-negative and the ER-positive groups, using the Cox regression model. The analysis was done at two cut-off levels of the receptors, 10 fmol/mg or 20 fmol/mq since with the receptor assays used, levels between 10–20 fmol/mg are considered equivocal. The results of the analysis are shown in Table 6. In the ER-positive group the risks of relapse were almost identical between PSA-positive and PSA-negative patients, which was expected since it is known that steroid hormone receptors are favourable prognostic indicators in breast cancer. However, in the ER-negative group, the risk of relapse was substantially reduced when the tumors were PSA-positive (hazards ratio 0.13–0.20). The difference was statistically significant when the cutoff level of the receptors was 20 fmol/mg due to the increase in the number of patients in this subgroup. The hazards ratio in the ER-negative subgroup remained very low even when nodal status, clinical stage and histological typewere controlled in the analysis.

Figure 6A:
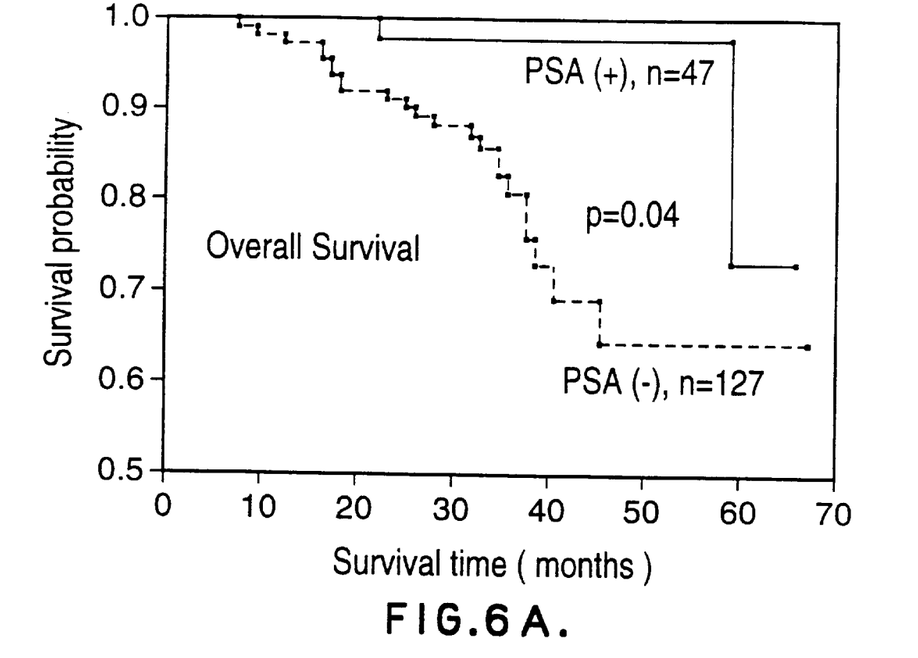
FIGS. 6A–B. Kaplan Meier Survival curves for PSA-positive and PSA-negative patients. Upper panel:: overall survival; lower panel: disease-free survival.
Figure 6B:
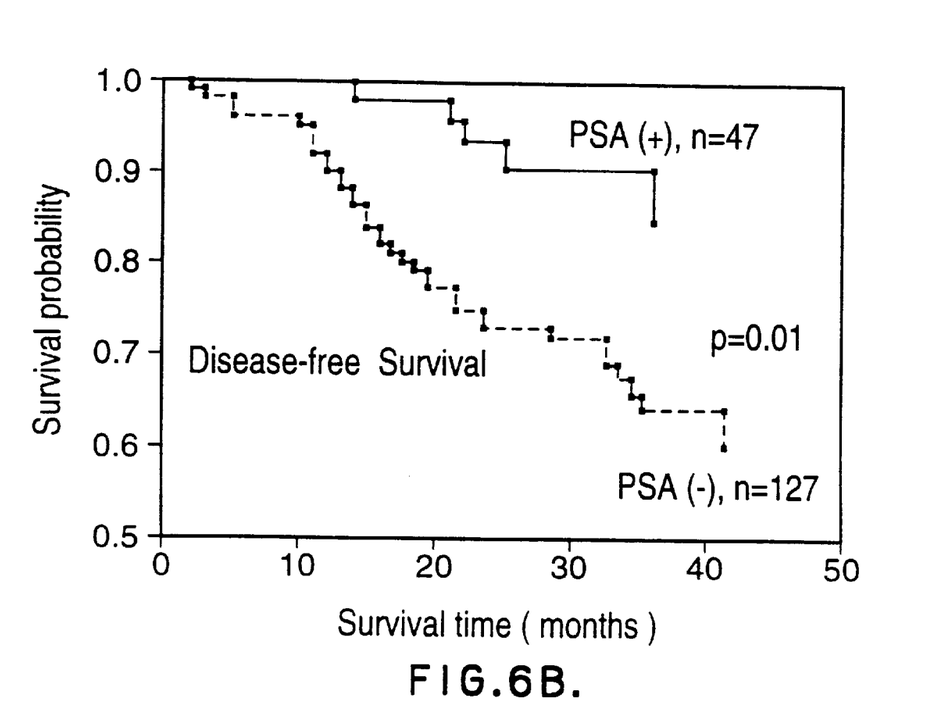

The risk for cancer relapse was significantly lower in patients with PSA-postive tumors than in patients with PSA-negative tumors. The hazard ratio for relapse of PSA-positive patients and PSA-negative patients was 0.32. A similar hazard ratio for overall survival was also observed. Overall and relapse-free survival curves are shown in FIG. 6. The probabilities of relapse-free and overall survivals were substantially higher in the PSA-positive patients than in the PSA-negative ones. FIG. 6 demonstrates that PSA-positive patients relapse less frequently and live longer than PSA-negative patients and that this difference is statistcally significant (P=0.06 and 0.04, respectively). Of the 174 patients, 42 had cancer relapse and 27 died. The overall follow-up time for these patients ranged between 7 and 67 months with a median of 33 months. PSA immunoreactivity higher than 0.03 ng/mg was detected in 27% of the patients (47/174). Without considering the follow-up time PSA-positive patients were less likely to relapse or die than PSA-negative patients (11% of PSA-positive patients versus 29% of PSA-negative patients for cancer relapse and 6% of PSA-positive patients versus 19% of PSA negative patients for death).

The data shows that breast tumors produce PSA, an antigen that was originally thought to be highly specific for the prostate. Previous immunohistochemical studies found no PSA immunoreactivity in breast or other tumors (17) or found occasional PSA immunoreactivity with polyclonal but not monoclonal antibodies, suggesting cross-reactivity effects (18).

The percentage of tumors producing PSA is significant (approximately 29%) similar or higher to the percentage of tumors with amplification of the HER-2 oncogene (19). The PSA form in the tumor has a molecular weight of approximately 30 KD and corresponds to the free PSA molecule.

Figure 5:
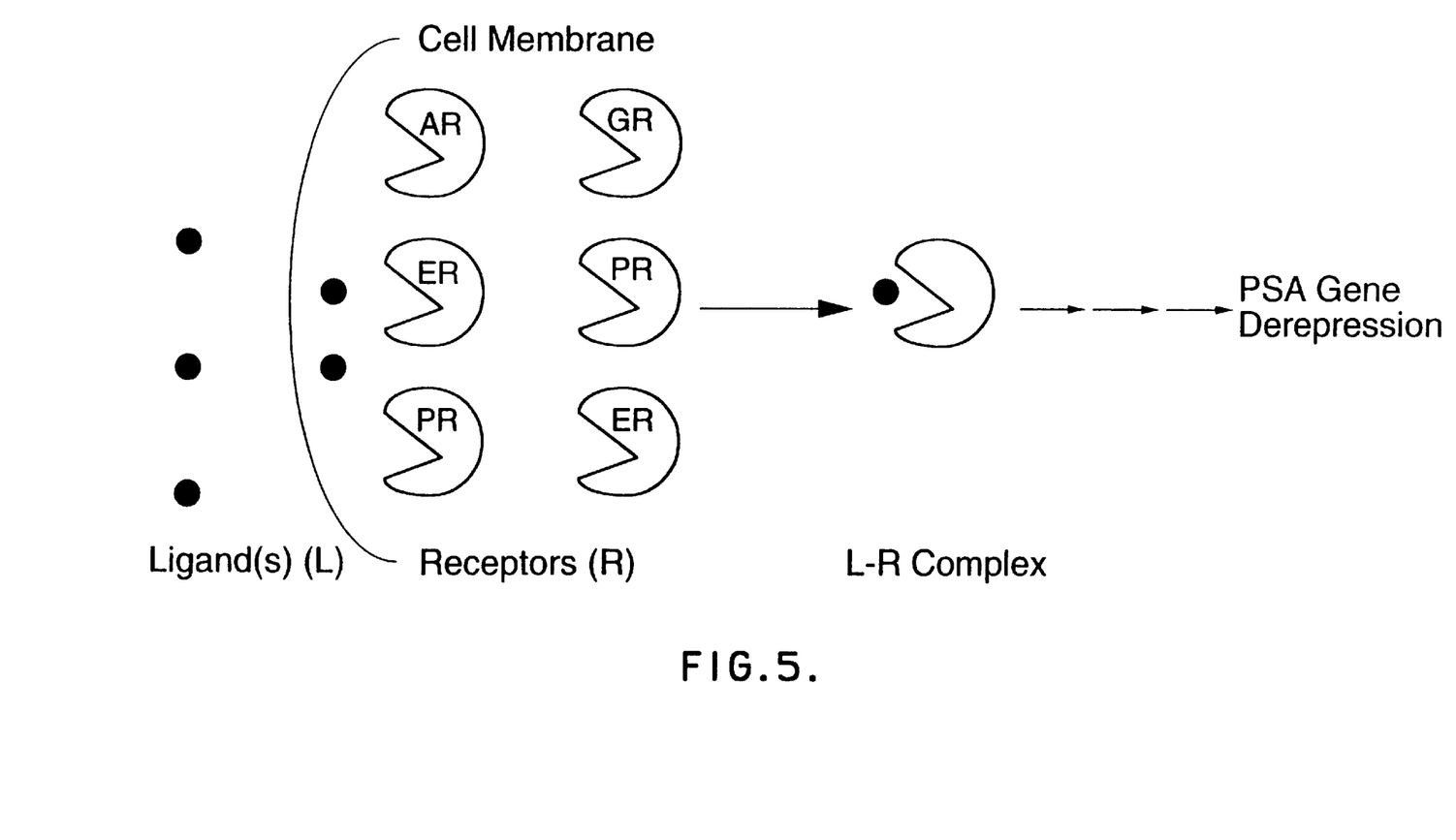

The production of PSA by breast tumors is due to PSA gene derepression by steroid hormone receptors bound to either estrogens, progestins or androgens (FIG. 5). This is indicated by the finding that most tumors producing PSA are steroid hormone receptor-positive. From the 151 PSA-positive tumors, only 20 were negative for estrogen and/or progesterone receptors. From these, fifteen had detectable estrogen and/or progesterone receptor levels but their concentration was below the cutoff point of 10 fmol/mg of protein. only five PSA-positive tumors (3.3%) had undetectable estrogen and progesterone receptor levels by the method used. In these five tumors the PSA immunoreactivity of the extracts was relatively low (0.05, 0.06, 0.14, 0.17 and 0.37 $\mu$g/L).

Recent reports suggest that PSA expression in the prostate may be under the direct influence of hormones, namely synthetic androgens or testosterone (20–23). Our observation that the presence of PSA in breast tumors is dependent upon the presence of the steroid hormone receptors and that there is no correlation between levels of PSA and receptors, indicate that the receptors are necessary but not sufficient for PSA production. In addition, one or more as yet unidentified ligands interact with the steroid hormone receptors to form a complex that regulates PSA gene derepression (FIG. 5). Active ligand-receptor complexes apparently exist in only 32% of the steroid hormone receptor-positive tumors. It is not clear if in the rest of the steroid hormone receptor-positive tumors the ligand(s) is/are absent, the receptors are defective as previously suggested (24) or the ligand-receptor complexes are formed but are somehow ineffective at the level of gene derepression.

This mechanism for PSA gene derepression in breast cancer is further supported by the finding that PSA production is associated with younger patient age (P=0.012, Table 3). In patients over the age of 55, only 24% of tumors produce PSA even if the estrogen or progesterone receptor-positive tumors are over 80% of the total. In patients under the age of 35, 33% of tumors produce PSA even if the estrogen and/or progesterone receptor-positive tumors are only 50% of the total. To further demonstrate the effect of age on PSA production the percentage of tumors that produce PSA from the total number of estrogen or progesterone receptor-positive tumors was calculated. These values are 67% (6/9) and 75% (6/8), respectively, for the age group<35 years and 29.7% (80/269) and 38.1% (30/210), respectively, for the age group>55 years (data from Table 3). The higher PSA positivity rate among younger patients may be related to production of the putative ligands of FIG. 5 by the functioning ovaries.

The higher PSA positivity rates among tumors which are positive for both estrogen and progesterone receptors and the intermediate positivity rates among tumors which are positive for only estrogen or only progesterone receptors, in comparison to the tumors which are negative for both receptors (Table II) demonstrate that either receptor can drive the production of PSA as seen in FIG. 5.

Although disease stage was available only for 203 patients, the association analysis between PSA production and disease stage demonstrates (Table IV and FIG. 4) that there is a clear trend for PSA-positive tumors to be preferentially associated with lower disease stage. The P values did not fall below 0.05 because of the relatively small number of samples in some patient groups.

A practical implication of these findings is that the PSA gene repression mechanism may be used for treatment of breast tumors. An examination of the ligands involved in steroid hormone receptor binding and PSA gene regulation in breast cancer may assist in this treatment. Breast tumors producing PSA constitute a sizable group (29% of patients) which may be examined in retrospective or prospective studies to establish if patients have a different prognosis or favourable response to selected therapy.

The data indicates that PSA is a favourable prognostic indicator because it is associated more strongly with tumors that are positive for both receptors, with lower disease stage and with improved patient survival (FIG. 6). In the breast tumor, PSA is present in the free 30 kD, presumably enzymatically active form. The suggested mode of PSA production (FIG. 5) based on the findings that the overwhelming majority of PSA-positive tumors have detectable receptors (146/151 or 97%) and that younger patients are more positive than older patients, lead to the conclusion that the PSA-positive tumor is a subgroup that possesses "effective" receptors, capable of gene regulation, as exemplified by PSA production. Then PSA-positive tumor patients will be most likely to respond to steroid hormone therapy. This was recently suggested for the steroid hormone receptor-inducible $pS_2$-BCEI protein, another potential prognostic indicator in breast cancer (25, 26).

A significant proportion of breast tumors (29%) produce PSA. PSA production is associated with steroid hormone receptor-positive tumors, younger age and earlier disease stage. PSA can be used as a routine prognostic marker for breast carcinoma and may play a role in disease initiation and progression. The invention's time-resolved fluoroimmunoassay is sensitive enough to detect levels of PSA as low as 0.05 µg/L in breast tumor extracts which equivalent to approximately 0.03 ng of PSA per mg of total protein.

METHODS

Patients—Breast Tumors

Approximately 500 breast tumor extracts were analyzed for steroid hormone receptors, for the p53 tumor suppressor gene product and for PSA, using the invention's new, highly sensitive immunofluorometric procedure.

All primary tumors used in this study were collected from about ten different hospitals in Ontario. Primary breast tumor tissue was immediately stored in liquid nitrogen after surgical resection, transported to the laboratory and stored subsequently at −70° C. until extraction was performed (~1–2 weeks). Approximately 0.5 g of tumor tissue was weighed out, smashed with a hammer if necessary, and pulverized in a Thermovac tissue pulverizer with liquid $N_2$. The resulting powder was transferred into 50 mL plastic tubes along with 10 mL of extraction buffer (0.01 mol/L Tris, 1.5 mmol/L ethylenediaminetetraacetic acid, 5 mmol/L sodium molybdate, pH adjusted to 7.40 with 5 mol/L HCl). The tissue powder was homogenized on ice with a single 58 burst of a Polytron homogenizer. The particulate material was pelleted by 1 h centrifugation at 105,000 g. The intermediate layer (cytosol extract) was collected without disturbing the lipid or particulate layers. Protein concentration of the cytosol extract was determined by the Lowry method and the extracts were stored at −70° C. until analysis (up to three weeks). In determining the total protein of tumor tissue sample to be tested, the protein concentration of the extract may provide the basis for such determination. Hence, the detection level of 0.03 ng of PSA per mg of total protein is determinative for deciding PSA (+ve) or (−ve). Stability studies have revealed that the p53 protein and PSA in the cytosol extracts are stable for at least four months at −70° C.

Estrogen and Progesterone Receptors

Quantitative analysis of estrogen and progesterone receptors (ER, PR) was measured using the Abbott enzyme immunoassay kits (Abbott Laboratories, North Chicago, Ill. 60064). The kits were used according to the manufacturer's instructions.

PSA and p53 Measurement

Analysis of PSA and p53 was performed using the invention's time-resolved fluoroimmunoassay.

Instrumentation

For measuring liquid-phase $Tb^{3+}$ fluorescence in white microtiter wells, we used the CyberFluor 615® Immunoanalyzer, a time-resolved fluorometer. The time-gate settings of the instrument and the interference filter in the emission pathway were the same as described elsewhere (32,33).

PSA MEASUREMENT

Reagents and Solutions

All reagents were purchased from Sigma unless otherwise stated. The coating solution was a 50 mmol/L 20 Tris buffer, pH 7.80, containing 0.5 g of sodium azide per litre. The wash solution was a 5 mmol/L Tris buffer, pH 7.80, containing 0.15 mol of NaCl and 0.5 g of polyoxyethylenesorbitan monolaurate (Tween 20) per litre.

The substrate buffer was a 0.1 mol/L Tris buffer, pH 9.1, containing 0.15 mol of NaCl, mmol $MgCl_2$ and 0.5 G of sodium azide per litre. The substrate stock solution is a 10 mmol/L diflunisal phosphate (DFP) solution in 0.1 mol/L NaOH. It is available from CyberFluor Inc., Toronto, Canada. The developing solution contains 1 mol Tris base, 0.4 mol NaOH, 2 mmol, $TbCl_3$ and 3 mmol of EDTA per litre (no pH adjustment). This solution is prepared as described previously (23, 24) and is commercially available by CyberFluor. The assay buffer is a 50 mmol/L Tris buffer, pH 7.80, containing 60 g of BSA, 0.5 mol of KCl, 0.5 g of sodium azide, 50 mL of normal mouse serum and 5 g of Triton X-100 per litre. The polyclonal biotinylated detection antibody and SA-ALP diluent is a 50 mmol/L Tris buffer, pH 7.80, containing 60 g of BSA per litre. The GARlg-ALP conjugate diluent is the same as the polyclonal biotinylated detection antibody diluent but also contains 4% (v/v) of goat serum. The blocking solution was a 50 mmol/L Tris buffer, pH 7.80, containing 10 g of BSA per litre.

Antibodies

The mouse monoclonal MBP0405 and the rabbit polyclonal PBG0101 anti-PSA antibodies were purchased from Medix Biotech, Foster City, Calif. 94404. The SA-ALP conjugate was purchased from Jackson ImmunoResearch, West Grove Pa. 193.90. The alkaline phosphatase-conjugated affinity purified goat anti-rabbit IgG, Fc fragment specific (GARlg-ALP) was also purchased from Jackson. A polyclonal rabbit antibody against $a_1$-antichymotrypsin was purchased from Dakopatts (Glostrup, Denmark).

Standards

Because of the unavailability of a universally accepted standard from PSA, for our studies we used PSA standards in a 50 mmol/L Tris buffer, pH 7.80, containing 6% (w/v) of BSA. A stock PSA solution, prepared from PSA purified from human seminal plasma, was purchased from aScripps Laboratories, San Diego, Calif. 92121. Our final standard solutions were calibrated against standards fro the Hybritech Tandem-PSA kit (Hybritech Inc., San Diego, Calif. 92126). For routine use we recommend six PSA standards with concentrations of 0, 0.025, 0.1, 0.5, 2 and 10 µg/L. These are stable for at least one month at 4° C.

Biotinylation of the Polyclanal Anti-PSA Antibody

The polyclonal anti-PSA antibody, purified by ion-exchange chromatography, was dialyzed overnight against five litres of a 0.1 mol/L sodium biocarbonate solution. This stock solution (≈2 mg/ml) was diluted 2-fold with a 0.5 mol/L carbonate buffer, pH 9.1. To this solution we added 1 mg of NHS-LC-Biotin (from Pierce Chemical Co., Rockford, Ill.) dissolved in 50 µL of dimethylsulfoxide, under continuous stirring and incubated for 2 h at room temperature. This biotinylated antibody was used without further purification and stored at 4° C. for at least six months.

Coating of Microtiter Wells

White, opaque 12-well microtiter polystyrene strips were obtained from Dynatech Laboratories, Alexandria, Va. 22314. The wells were coated overnight at room temperature with 500 ng/100 µL/well of coating monoclonal anti-PSA antibody in the coating buffer. Before use, the wells were washed×2 and blocked for 1 hour with 200 µL/well of the blocking solution.

Assay Procedure

Wash the strips×6. In each well pipet 50 µL of tumor tissue extract or PSA standards and add 50 µL of assay buffer per well. Incubate for 3 h at room temperature with continuous mechanical shaking and wash×6. Add 100 µL per well of the biotinylated polyclonal rabbit detection antibody diluted 1,000-fold in the polyclonal detection antibody diluent (100 ng of antibody per well). Incubate for 1 h as above and wash×6. Add 100 µL per well of SA-ALP conjugate diluted 30,000-fold in the SA-ALP diluent (3 ng of conjugate per well). Incubate for 15 min as above and wash×6. Add 200 µL/well of the DFP substrate diluted 10-fold just before use in the substrate buffer (working DFP substrate solution is 1 mmol/L) and incubate for 10 min at room temperature with shaking. Add 100 µL/well of the developing solution, mix by shaking for 1 min and read the $Tb^{3+}$-specific fluorescence with the CyberFluor 614 Immunoanalyzer. Data reduction is automatic. Assay of the PSA-$a_1$-Antichymotrypsin Complex (PSA-ACT)

This assay is exactly the same as the PSA assay described above but instead of using the biotinylated polyclonal rabbit anti-PSA antibody, we used the polyclonal rabbit $a_1$-antichymotrypsin antibody, diluted 500-fold in the SA-ALP conjugate diluent. We then added 100 µL of a 5,000-fold diluted FARlg-ALP conjugate (20 ng per well) and incubated for 30 min with shaking. After washing×6, we completed the assay by adding the DFP substrate as described in the PSA assay. No effort was made to calibrate this assay because of the unavailability of standard PSA-ACT complex.

PSA was also measured in selected tumor extracts with commercially available kits (a). The Hybritech Tandem®-R PSA kit (Hybritech Inc, San Diego, Calif. 92126), (b). The IRMA-CountSPSA kit (Diagnostic Products Corp., Los Angeles, Calif. 90045) and (c). The Abbott $IM_x$® automated PSA method (Abbott Laboratories, Chicago, Ill., U.S.A.). High performance liquid chromatography was performed with a Shimadzu system with an absorbance monitor at 280 nm (Shimadzu Corp., Kyoto, Japan), isocratically, using a mobile phase of 0.1 mol/L $NaH_2SO_4$–0.1 mol/L $NaH_2PO_4$, pH 6.80. Flow rate was 0.5 mL/min. The gel filtration column used was a Bio-Sil SEC-400, 600 mm×7.5 mm (BioRad Labs, Richmond, Calif.). The column was calibrated with a molecular weight standard solution from BioRad, containing thyroglobulin (670 KD), IgG (158 KD) ovalbumin (44 KD), myoglobin (17 KD) and cyanocobalamin (1.4 KD). Fractions of 0.5 mL each were collected with a fraction collector, Model FRAC-100 (Pharmacia, Uppsala, Sweden) after injecting a 150 mL sample.

Statistical Analysis

The chi-square ($X_2$) test was used to determine the statistical significance of differences in distributions and all chi-square values and the corresponding P values were calculated by the statistical software SAS (SAS Institute Inc., Cary, N.C., USA).

p53 Measurement

Solutions and Reagents

Lysis buffer: 150 mM CaCl, 20 mM Tris, 1% Nonidet P-40. 0.5 mM phenylmethysulfonylchloride (PMSF). 1 µg $ml^{-1}$ leupeptin. 50 g $ml^{-1}$ aprotinin. Sample diluent (diluent for cell lysates, serum, polyclonal anti-ps rabbit antiserum and alkaline phosphatase-conjugated goat anti-rabbit antibody): 50 mM Tris, pH 7.40, containing 60 g bovine serum albumin (BSA) and 1 g sodium azide per litre. Monoclonal anti-$p^{53}$ antibody diluent; 50 mM Tris, pH 7,40, containing 60 g bovine serum albumin, 1 g sodium azide and 0.5 mol KCl per litre.

Substrate buffer 0.1 M Tris, pH 9.1, 0.15 M NaCl, 1 mM $MgCl$. Developing solution: $2\times10^{-3}$, $TbCl_3$, $3\times10^{-3}$ EDTA. 0.4 M NaOH, 1M Tris base (no Ph adjustments). Prepare as described elsewhere (32). Wash solution: Distilled water.

Coating buffer: 50 mM Tris, pH 7.80, containing 1 g of sodium azide per litre. The phosphate ester of 5-fluorosalicylic acid (FSAP) was obtained from CyberFluor Inc., Toronto, Canada. It is stored as a 10 mM stock solution in 0.1 M NaOH at 4° C. for many months. This stock is diluted 10-fold in the substrate buffer just before use. All other chemicals were from Sigma Chemical Co., St. Louis Mo., USA, except Nonidet P-40 (Boehringer-Mannheim, Indianapolis, Ind., USA) $TbCl_3 \cdot 6H_2O$ IGFS Chemicals, Columbus, Ohio, USA) and the biotinylation reagent NHS-LC-Biotin (Pierce Chemical Co., Rockford, Ill., USA).

p53 Standards

Recombinant mutant human p53 protein standards in the range from 0.25–4 ng $ml^{-1}$ were obtained from-Oncogene Science, Inc., Uniondale, N.Y., USA and were considered the primary standards. These standards were used to optimize the assay and standardize cell lysates for subsequent studies. Another human wild-type recombinant p53 solution, prepared as described elsewhere (33) was a gift to us by Dr. C. Prives, Columbia University. This p53 preparation was diluted in the sample diluent to make standard solutions.

Antibodies

The mouse anti-p53 monoclonal antibodies, PAb 421 and PAB 240 were kindly provided by Dr. S. Behchimol, Ontario Cancer Institute. These are tissue culture supernatants containing approximately 30 µg ml antibody. The rabbit polyclonal anti-p53 antibody, CM-1, was obtained from Dimension Labs, Mississauga, Ontario, canada. The goat anti-rabbit antibody, conjugated to alkaline phosphatase and the goat anti-mouse antibody, $F_c$ specific, both approximately 1 mg $ml^{-1}$, were obtained from Jackson Immunoresearch, West Grove, Pa., USA.

Immunoassay of p53

White, opaque, 12-well microtiter strips (Dynatech Labs, Alexandria, Calif.<USA) were coated with a goat anti-mouse antibody by pipetting 100 µl 500 ng $well^{-1}$ of the antibody solution in the coating buffer. After overnight incubation at room temperature, the wells were washed four times with distilled water. The wells were then blocked by pipetting 200 µl well of the sample diluent, incubating for 1 h and washing as above. The wells were then used for the assay as follows. We add 100 ng $well^{-1}$ of mouse monoclonal anti-pt3 antibody (PAb 421 or PAb 240) and 50 µl of sample (p53 standards of cell lysates). The antibodies are cell culture supernatants containing about 30 µg ml of antibody and they were diluted×20 in the monoclonal anti-p53 antibody diluent. The cell lysates were used in different dilutions in the sample diluent, varying from 10–1000-fold. After 3 h incubation with shaking at 37° C., the plates were washed×4. We then added 100 µl well of the polyclonal rabbit anti-p53 antibody (diluted 5000-fold in the sample diluent) and incubated with shaking for 1 h at room temperature. After washing×4, we added 100 µl wellof the goat anti-rabbit alkaline phosphatase conjugate solution (diluted 5000-fold in the sample diluent) and incubated with shaking for 1 h at room temperature. The strips were washed again×4 and 100 µl $well^{-1}$ of the FSAP solution ($10^{-3}$ M in the substrate buffer_were added and incubated for 10 min with shaking at room temperature. The fluorescent complex was then formed by adding 100 µl well of the developing solution followed by brief mixing for 1 min. Time=resolved fluorometric measurements at 615 nm were performed on the CyberFluor 615 Immunoanalyzer. Data reduction and plotting of calibration curves was automatic through the analyzer software. Detection of PSA R Detection of PSA mRNA can be accomplished by the method of Deguchi et al or a modification of it. This method involves isolation of mRNA from tumors, synthesis of cDNA by reverse transcription and PCR amplification of the cDNA using PSA specific primers. The sequence of primers used are as follows:

5'- TCG-GCA-AGT-TCA-CCC-TCA-3'
5'- CCC-TCT-CCT-TAC-TTC-ATC-C-3'.

PCR amplification produces a fragment of 754 base pairs which is electrophoresed on agarose gels and Southern blotted to Hybond N+ membrane. A probe (5'- GGA-ACC-TTG-GAA-ATG-ACC-AG-3') labeled with fluorescein is added to hybridize with cDNA for PSA. The probe is detected using chemiluminescence reagents from Amersham International.

Breast Cancer Survival and ER-negative, PSA-positive Study

One hundred and seventy four patients with primary breast cancer were included in this study. All patients were treated and followed at the Department of Gynecologic Oncology at the University of Turin. Ages of these patients ranged from 25 to 91 years with a median of 56 years. Thirty two percent of the patients were<50 years and 69%>50 years. The follow-up time ranged from 7 to 67 months with a median of 33 months.

Clinical and pathological information, including clinical stage, histological cell type and grade, axillary node involvement, tumor size, presence of ER and PR in tumor cells and adjuvant treatment after surgery, was collected for each patient. According to the TNM staging system, 45%, 47% and 8% of the patients had stage I, II and III or IV, respectively. Each breast cancer specimen was also histologically graded and typed. Thirty nine percent of patients had low grade (I), 42% had moderate grade (II), and 19% had high grade (III). Seventy percent of patients had ductal carcinomas. The rest had lobular (13%), lobular in situ (2%), medullary (5%), papillary (2%), tubular (2%), tubulo-lobular (3%), or unknown types (3%). In the data analysis, histological type was grouped into two categories, i.e. ductal versus non-ductal, because of the small number of patients who had types other than ductal carcinomas.

The size of tumor in these patients ranged from 0.7 to 6 cm, and median and mean sizes were identical, 2.4 cm. Fiftyone percent of the patients had tumor invading the axillary lymph nodes. Of the 174 patients, 56% were treated with adjuvant therapy as follows: tamoxifen (37%), chemotherapy (15%), or both (4%). The rest (44%) received no further treatment after surgery.

Demographic, clinical and pathological variables, including age, clinical stage, histological grade and type, nodal status, tumor size, ER and PR, and adjuvant treatment, were compared between PSA-positive and PSA-negative groups, using the contingency table and Chi-square test in order to examine the associations between PSA and these variables. The relationship between each of the study variables and relapse-free or overall survival was expressed by the hazard ratio and its 95% confidence interval, which was calculated univariately using the Cox proportional hazard regression model (35). The multivariate Cox regression model was also employed to evaluate the impact of PSA immunoreactivity on patient survival while controlling for other clinical and pathological variables which may also affect the survival, such as clinical stage (I, II or III/IV), nodal status (positive or negative), tumor size (greater or less than mean size), steroid hormone receptors (presence or absence), and adjuvant treatment (none, tamoxifen, or both tamoxifen and chemotherapy). Kaplan-Meier relapse-free and overall survival curves (36) were constructed to demonstrate the survival difference between PSA-positive and negative groups. The logrank test (37) was used to examined the significance of the differences between survival curves.

Although preferred embodiments of the invention are described herein in detail, it will be understood by those skilled in the art that variations may be made thereto without departing from the spirit of the invention or the scope of the appended claims.

TABLE I

Analysis of PSA in Breast Tumor Extracts

| | PSA, mg/L | | | |
|---|---|---|---|---|
| Number of Patients | <0.05 | ≧0.05 | ≧0.10 | ≧0.30 |
| 525 | 374 | 151 | 96 | 49 |
| % of Samples | 71.2% | 28.8% | 18.3% | 9.3% |

TABLE II

Relationship Between Estrogen and Progesterone Receptors, PSA and p53 Levels in Breast Tumor Extracts[1]

| | PSA (+) (%) | PSA (−) (%) | P Value |
|---|---|---|---|
| Samples (N = 525) | | | |
| ER (+) 393 | 127 (32.3) | 266 (67.7) | |
| ER (−) 132 | 24 (18.2) | 108 (81.8) | 0.002 |
| PR (+) 321 | 111 (34.6) | 210 (65.4) | |
| PR (−) 204 | 40 (19.6) | 164 (80.4) | <0.001 |
| ER (+) or PR (+) 407 | 131 (32.2) | 276 (67.8) | |
| ER (−) and PR (−) 118 | 20 (16.9) | 98 (83.1) | 0.001 |
| ER (+) and PR (+) 307 | 107 (34.8) | 200 (65.2) | |
| ER (+) and PR (−) 86 | 20 (23.3) | 66 (76.7) | |
| ER (−) and PR (+) 14 | 4 (28.6) | 10 (71.4) | |
| ER (−) and PR (−) 118 | 20 (16.9) | 98 (83.1) | 0.002 |

| | p53 (+) (%) | p53 (−) (%) | |
|---|---|---|---|
| Samples (N = 558) | | | |
| ER (+) 416 | 64 (15.4) | 352 (84.6) | <0.001 |
| ER (−) 142 | 50 (35.2) | 92 (64.8) | |
| PR (+) 338 | 47 (13.9) | 291 (86.1) | <0.001 |
| PR (−) 220 | 67 (30.4) | 153 (69.6) | |
| ER (+) or PR (+) 428 | 68 (15.9) | 360 (84.1) | <0.001 |
| ER (−) and PR (−) 130 | 46 (35.4) | 84 (64.6) | |
| Samples (N = 474) | | | |
| PSA (+) 90 | 20 (22.2) | 70 (77.8) | P =0.37 |
| PSA (−) 384 | 103 (26.8) | 281 (73.2) | |

[1]For negativity cutoff levels see text. Values in brackets are percentages.

TABLE III

Distribution of PSA-Positive, Estrogen Receptor-Positive and Progesterone Receptor-Positive Tumors in Various Age Groups

| | % of Positive Tumors[1] | | |
|---|---|---|---|
| Patient Age (Years) | PSA (+) | ER (+) | PR (+) |
| <35 (N = 18) | 33.3 (6/18) | 50.0 (9/18) | 44.4 (8/18) |
| 35–44 (N = 66) | 36.4 (24/66) | 71.2 (47/66) | 62.1 (41/66) |

TABLE III-continued

Distribution of PSA-Positive, Estrogen Receptor-Positive and Progesterone Receptor-Positive Tumors in Various Age Groups

| Patient Age (Years) | PSA (+) | % of Positive Tumors[1] ER (+) | PR (+) |
|---|---|---|---|
| 45–54 (N = 104) | 38.5 (40/104) | 64.4 (67/104) | 58.7 (61/104) |
| >55 (N = 336) | 23.8 (80/336) | 80.1 (269/336) | 62.5 (210/336) |
| P Value(2) | 0.012 | 0.001 | 0.45 |

[1]In brackets are numbers of positive tumors per total number of tumors in each group. N = number of patients per group.
(2)P value for comparing the distribution of positive or negative tumors for each parameter, in the various age groups.

TABLE IV

Association of PSA-Positive Tumors with Disease Stage

| Disease Stage | % of PSA-Positive Tumors[1] |
|---|---|
| 0 | 42.9 (6/14) |
| 1 | 30.7 (35/114) |
| 2 | 22.0 (13/59) |
| 3 | 12.5 (2/16) |
| P | 0.18 |
| 0–1 | 32.0 (41/128) |
| 2–3 | 20.0 (15/75) |
| P | 0.06 |

[1]In brackets are numbers of positive tumors per total number of tumors in each group.

TABLE V

Relationship between PSA Immunoreactivity and ER & PR

| Receptor Status | No. of Patients | No. of PSA + | OR & 95% CI | p value |
|---|---|---|---|---|
| ER−, PR− | 226 | 32 (14%) |  | 1.00 |
| ER+, PR− | 139 | 28 (20%) | 1.53 (0.88–2.67) | 0.13 |
| ER−, PR+ | 58 | 24 (41%) | 4.28 (2.25–8.14) | <0.01 |
| ER+, PR+ | 852 | 302 (35%) | 3.33 (2.23–4.96) | <0.01 |

OR: Odds ratio
CI: Confidence interval.

TABLE VI

Associations between PSA and relapse-free survival stratified by the status of estrogen receptors

| ER status | PSA(+) patients | Hazards ratio[1] | 95% confidence Interval | P value |
|---|---|---|---|---|
| ER cutoff at 10 fmol/mg |  |  |  |  |
| Univariate analysis |  |  |  |  |
| ER(+) (n = 112)[2] | 36 | 0.98 | 0.37–2.61 | 0.97 |
| ER(−) (n = 57) | 9 | 0.16 | 0.02–1.22 | 0.08 |
| Multivariate analysis[3] |  |  |  |  |
| ER(+) (n = 112) | 36 | 0.80 | 0.27–2.32 | 0.68 |
| ER(−) (n = 57) | 9 | 0.13 | 0.02–1.15 | 0.07 |
| ER cutoff at 20 fmol/mg |  |  |  |  |
| Univariate analysis |  |  |  |  |
| ER(+) (n = 95) | 27 | 1.42 | 0.46–4.34 | 0.54 |
| ER(−) (n = 74) | 18 | 0.18 | 0.04–0.76 | 0.02 |
| Multivariate analysis[3] |  |  |  |  |
| ER(+) (n = 95) | 27 | 0.96 | 0.27–3.33 | 0.94 |
| ER(−) (n = 74) | 18 | 0.20 | 0.04–0.93 | 0.04 |

[1]The ratio of hazards between PSA-positive and PSA-negative patients.
[2]N = number of patients.
[3]Adjusted for age, clinical stage, nodal status, tumor size, and histological grade.

REFERENCES

1. Harris, J. R., Lippman, M. E., Veronesi, U., Willett, W. Breast cancer, (first of three parts). New Engl. J. Med., 1992; 327: 319–28.
2. Harris, J. R., Lippman, M. E., Veronesi, U., Willett, W. Breast cancer, (second of three parts). New Engl. J. Med., 1992; 327: 390–8.
3. Harris, J. R., Lippman, M. E., Veronesi, U., Willett, W. Breast cancer, (third of three parts). New Engl. J. Med., 1992; 327: 473–80.
4. McGuire, W. L., Clark, G. M. Prognostic factors and treatment decisions in axillary node-negative breast cancer. New Engl. J. Med., 1992 326: 1756–61.
5. McGuire, W. L., Tandon, A. K., Craig Alfred, D., Chamness, G. C., Clark, G. M. How to use prognostic factors in axillary node-negative breast cancer patients. J. Natl. Cancer Inst., 1990; 82: 1006–15.
6. Muss, H. B. Endocrine therapy for advanced breast cancer: a review. Breast Cancer Res. Treat., 1992; 21: 15–26.
7. Carter, H. B., Coffey, D. S. The prostate: an increasing medical problem. The Prostate, 1990; 16: 39–48.
8. Nomura, A. M. Y., Kolonel, L. N. Prostate cancer: A current perspective. Am. J. Epidemiol., 1991; 13: 200–27.
9. Bruchovsky, N., Brown, E. M., Coppin, C. M., et al. The endocrinology and treatment of prostate tumor progression. Prog. Clin. Biol. Res., 1987; 239: 347–57.
10. Thompson, T. C. Growth factors and oncogenes in prostate cancer. Cancer Cells, 1990; 2: 345–354.
11. Oesterling, J. E. Prostate specific antigen: a critical assessment of the most useful tumor marker for adenocarcinoma of the prostate. J. Urol., 1991; 145: 907–923.
12. Diamandis, E. P. Immunoassays with time-resolved fluorescence spectroscopy. Principles and applications. Clin. Biochem.,1988; 21: 139–150.
13. He, Y., Diamandis, E. P. Ultrasensitive time-resolved immunofluorometric assay of prostate-specific antigen in serum. clin. Chem., 1993 (in press).
14. Hassapoglidou, S., Diamandis, E. P., Sutherland, D. J. A. Quantification of p53 protein in tumor cell lines, breast tissue extracts and serum with time-resolved immunofluorometry. Oncogene, 1993 (in press).
15. Stenman, U. H., Leinonen, J., Alfthan, H., Rannikko, S., Tuhkanen, K., Alfthan, O. A complex between prostate-specific antigen and $a_1$-antichymotrypsin is the major form of prostate-specific antigen in serum of patients with prostatic cancer: Assay of the complex improves clinical sensitivity for cancer. Cancer Res., 1991; 51: 222–6.

16. Lilja, H., Christensson, A., Dahlen, U., et al. Prostate-specific antigen in serum occurs predominantly in complex with a₁-antichymotrypsin. Clin. Chem., 1991; 37: 1618–25.

17. Ford, T. F., Butcher, D. N., Masters, J. R. W., Parkinson, C. M. Immunocytochemical localisation of prostate-specific antigen: specificity and application to clinical practice. British J. Urol., 1985; 57: 50–5.

18. Papotti, M., Paties, C., Peveri, V., Moscuzza, L., Bussolati, G. Immunocytochemical detection of prostate-specific antigen (PSA) in skin adnexal and breast tissues and tumors. Bas. Appl. Histochem., 1989; 33: 25–9.

19. Slamon, D. J., Clark, G. M., Wong, S. G. et al. Human breast cancer: correlation of relapse and survival with amplification of the HER-2/neu oncogene. Science, 1987; 235: 177–82.

20. Wolf, D. A., Schulz, P., Fittler, F. Transcriptional regulation of prostate kallikrein-like gene by androgen. Mol. Endocrinol., 1992; 6:753–62.

21. Henttu, P., Liao, S. S., Vihko, P. Androgens up-regulate the human prostate-specific antigen messenger ribonucleic acid (mRNA) but down-regulate the prostatic acid phosphatase MRNA in the LNCaP cell line. Endocrinology, 1992; 130: 766–72.

22. Montgomery, B. T., Young, C. Y., Bilhartz, D. L., Andrews, P. E., Prescott, J. L., Thompson, N. F. Hormonal regulation of prostate-specific antigen (PSA) glycoprotein in the human prostate adenocarcinoma cell line, LNCAP. Prostate, 1992; 21: 63–73.

23. Weber, J. P., Oesterling, J. E., Peters, C. A., Partin, A. W., Chan, D. W., Walsh, P. C. The influence of reversible androgen deprivation on serum prostate-specific antigen levels in men with benign prostate hyperplasia. J. Urol., 1989; 141: 987–91.

24. Wei, L. L. Transcriptional activation of the estrogen receptor. Clin. Chem., 1993; 39: 341–45.

25. Milgrom, E. The oestrogen-regulated pS₂-BCEI protein in breast cancer. In: Goldhirsch, A., ed. Endocrine therapy of breast cancer V. Berlin: Springer Verlag, 1992: 17–22.

26. Foekens, J. A., Rio, M. C., Seguin, P., et al. Prediction of relapse and survival in breast cancer patients by PS2 protein status. Cancer Res.,1990; 50: 3832–7.

27. Rochefort, H. Cathepsin D in breast cancer. Breast Cancer Res. Treat., 1990; 16: 1–13.

28. Silvestrini, R., Veneroni, S., Benini, E., DiFronzo, G., Daidone, M.G. p53 and cathepsin D are independent of established prognostic factors in breast cancer. Int. J. Oncol. 1992; 1: 507–12.

29. Allred, D. C., et al. Association of p53 Protein Expression with Tumor Cell Proliferation Rate and Clinical Outcome in Node-Negative Breast Cancer. J. Natl. Cancer Inst. 1993; 85: 200–206.

30. Thor, A. D., et al. Accumulation of p53 Tumor Suppressor Gene Protein: An Independent Marker of Prognosis in Breast Cancers. J. Natl Cancer Inst. 1992; 84: 845–855.

31. Henderson, I. C. (1991). In Breast Diseases, Harris, J. R., Hellman, S., Henderson, I. C., Kinne, D. (eds). J.P. Lippincott: Philadelphia. pp. 332–346.

32. Christopoulos, T. K. and Diamandis, E. P. (1992) Ana. Chem. 64:342–346.

33. Wang, E. H., Friedman, P. N., and Prices, C (1989) Cell 57:379–392.

34. Deguchi, T. et al. (1993) Cancer Research 53:5350–5354.

35. Cox, D. R. J. R. Stat Soc(B) 1972; 34: 187–202.

36. Kaplan, E. L. Meier, P. J. Am. Stat. Assoc. 1958; 53: 457–481.

37. Mantel, N. Cancer Chemother Rep 1966; 50: 163–170.

What is claimmed is:

1. A method for prognosing breast carcinoma in female breast tumor tissue, said method comprising:

i) detecting the presence of prostate-specific antigen (PSA) MRNA in a sample of breast tumor tissue; and ii) upon detecting PSA mRNA in said sample, classifying said sample as PSA expression positive which indicates a favorable prognosis for breast cancer.

2. A method according to claim 1, wherein the sample has been cryogenically frozen.

3. A method according to claim 1, wherein classifying said sample as PSA expression positive indicates hormonal treatment for said breast carcinoma.

4. A method according to claim 1, wherein the detecting of PSA MRNA is by PCR amplification.

5. A method according to claim 1 wherein the detecting of PSA MRNA is by Northern blotting.

6. A method according to claim 1, wherein said PSA present in the breast tumor tissue is free PSA MRNA.

7. A method for indicating treatment of breast carcinoma in female breast tumor tissue, said method comprising:

i) detecting the expression of prostate-specific antigen (PSA) MRNA in a sample of breast tumor tissue; and ii) upon detecting PSA mRNA in said sample classifying said sample as PSA expression positive wherein PSA positive expression indicates hormonal treatment for said breast carcinoma.

* * * * *

UNITED STATES PATENT AND TRADEMARK OFFICE
CERTIFICATE OF CORRECTION

PATENT NO.     : 6,261,766 B1
DATED          : July 17, 2001
INVENTOR(S)    : Eleftherois Diamandis It is certified that error appears in the above-identified patent and that said Letters Patent is hereby corrected as shown below:

<u>Title page,</u>
Item [22], Filed: "September 26, 2001" has been replaced with -- July 28, 1997 --, <u>Column 18,</u>
Line 1, insert -- protein --, after the word "PSA"
Line 2, delete "MRNA" and insert -- mRNA --,
Line 2, delete "MRNA" and insert -- mRNA --,
Line 4, delete "MRNA" and insert -- mRNA --,
Line 4, delete "MRNA" and insert -- mRNA --, Signed and Sealed this Seventeenth Day of September, 2002

Attest:

Attesting Officer

JAMES E. ROGAN
*Director of the United States Patent and Trademark Office*